(12) United States Patent
Barclay et al.

(10) Patent No.: US 7,582,317 B2
(45) Date of Patent: Sep. 1, 2009

(54) FOOD SUPPLEMENTS COMPRISING, AS A HEALTH COMPONENT, SARGAHYDROQUINOIC ACID OR DERIVATIVE THEREOF

(75) Inventors: Scott Sinclair Barclay, Sharnbrook (GB); John Anthony Bosley, Sharnbrook (GB); Frederick William Cain, Wormerveer (NL); Claudia Koenen, Wormerveer (NL); Julia Sarah Rogers, Sharnbrook (GB); Ulrike Schmid, Wormerveer (NL)

(73) Assignee: Loders Croklaan USA LLC, Channahon, IL (US)

( * ) Notice: Subject to any disclaimer, the term of this patent is extended or adjusted under 35 U.S.C. 154(b) by 789 days.

(21) Appl. No.: 10/230,352

(22) Filed: Aug. 29, 2002

(65) Prior Publication Data

US 2003/0129294 A1    Jul. 10, 2003

(30) Foreign Application Priority Data

| Sep. 4, 2001 | (EP) | ................................. 01307523 |
| Mar. 4, 2002 | (EP) | ................................. 02251500 |

(51) Int. Cl.
- *A61K 36/00* (2006.01)
- *A01N 65/00* (2006.01)
- *A01N 61/00* (2006.01)
- *A61K 31/00* (2006.01)
- *C09K 15/00* (2006.01)

(52) U.S. Cl. ........................... 424/776; 252/404; 514/1
(58) Field of Classification Search ...................... None
See application file for complete search history.

(56) References Cited

U.S. PATENT DOCUMENTS

| 3,615,588 | A | * | 10/1971 | Heine et al. ................. 426/607 |
| 4,451,488 | A | * | 5/1984 | Cook et al. ................... 426/89 |
| 5,674,900 | A | | 10/1997 | Ubillas et al. | |
| 6,267,985 | B1 | * | 7/2001 | Chen et al. ................... 424/451 |
| 6,489,494 | B1 | | 12/2002 | Leonard | |
| 6,713,512 | B1 | | 3/2004 | Leonard | |

FOREIGN PATENT DOCUMENTS

| JP | 61-043132 | 3/1986 |
| JP | 08-169826 | 7/1996 |
| JP | 09-118665 | 5/1997 |
| WO | WO 96/39130 | 12/1996 |
| WO | WO 99/52508 | 10/1999 |

OTHER PUBLICATIONS http://www.henriettesherbal.com/eclectic/kings/strophantus.html (From: King's American Dispensatory, Published: 1898).*
Lok CM, Groenewegen A, Stroink JBA, Ward JP. Phytochemistry. 1983; 22(9): 1973-1976.*
http://www.henriettesherbal.com/eclectic/bpc1911/strophanthus.html (From: The British Pharmaceutical Codex. Published: 1911).*
http://www.henriettesherbal.com/eclectic/kings/pilula.html (From: King's American Dispensatory, Published: 1898).*
M. Segawa et al., "New Plastoquinones from the Brown Alga Sargassum Sagamianum Var. Yezoense", Chemistry Letters, Chemical Society of Japan, Tokyo, JP, 1987, pp. 1365-1366, XP002938985.
C. M. Lok et al., "Kombic Acid, A Hydroquinone Polyisoprenoic Carboxylic Acid From *Pycnanthus Kombo* Seed Fat". Pytochemistry (Oxford), vol. 22, No. 9, 1983, pp. 1973-1976. XP001056549.
Luo et al., The Journal of Pharmacology and Experimental Therapeutics, 288(2):529-534 (1999).
Perez-Castorena et al., Planta Med, 68:645-647 (2002).
Fort et al., J. Org. Chem., 65:6534-6539 (2000).

* cited by examiner

*Primary Examiner*—Christopher R Tate
*Assistant Examiner*—Amy L Clark
(74) *Attorney, Agent, or Firm*—Morgan Lewis & Bockius LLP (57) ABSTRACT

The invention concerns blends of a hydroquinone substituted poly unsaturated fatty acid (as present in Kombo nut oil) or a derivative thereof, which blends comprised:

(i) 0.1-99.9 wt % of the substituted acid
(ii) 0-99.8 wt % of Kombo butter glycerides
(iii) 0.1-99.9 wt % of other triglycerides Food products and food supplements comprising such hydroquinone substituted acids are also part of the invention. The substituted acids display many useful health benefits.

9 Claims, 6 Drawing Sheets

Figure 5:
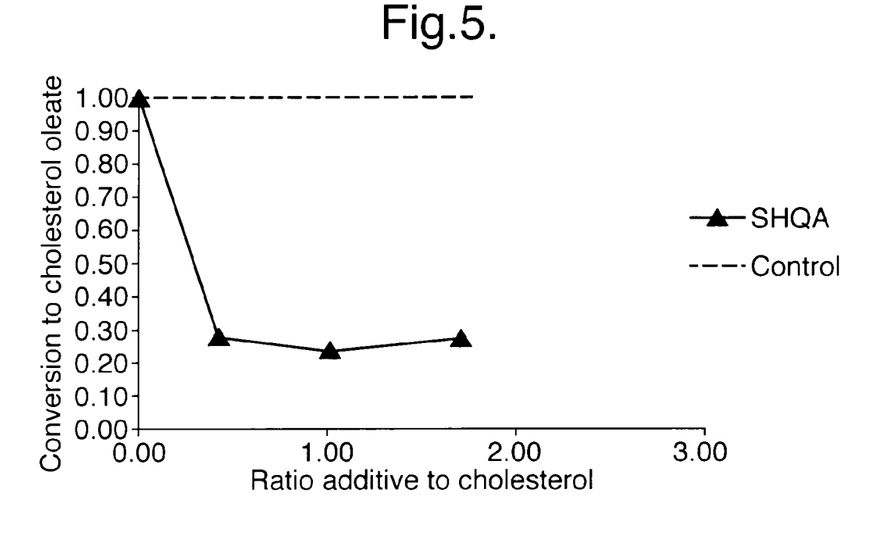
Figure 5A:
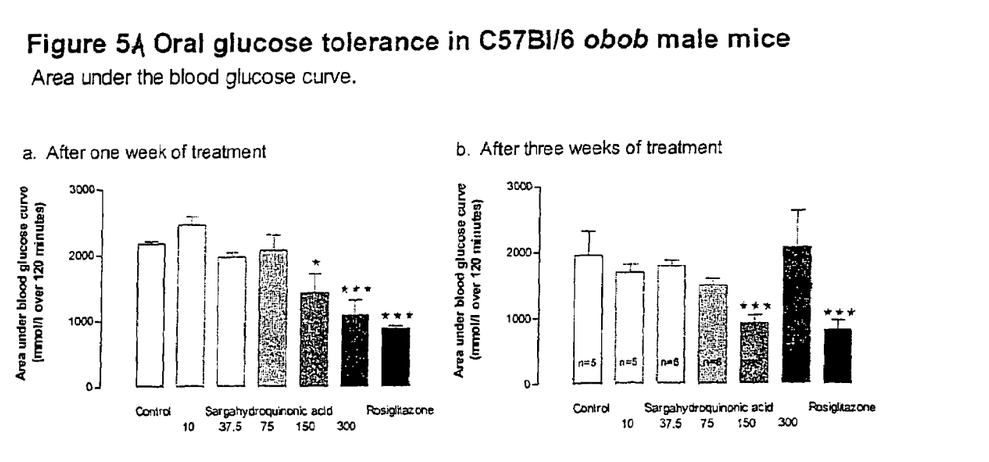

Figure 5A Oral glucose tolerance in C57Bl/6 *obob* male mice
Area under the blood glucose curve.

a. After one week of treatment b. After three weeks of treatment

Fig.5.

Fig.6.

Figure 6:
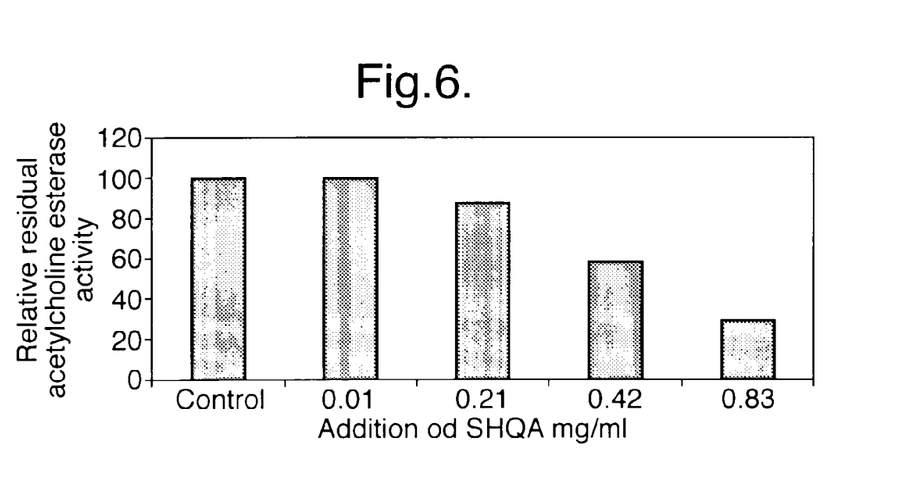
Figure 6A:
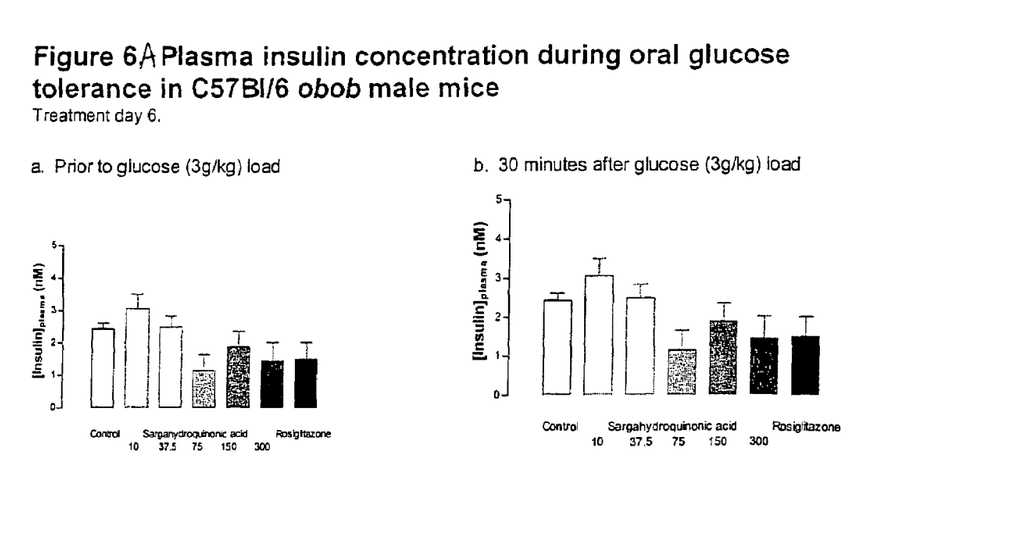

Figure 6A Plasma insulin concentration during oral glucose tolerance in C57Bl/6 *obob* male mice
Treatment day 6.

a. Prior to glucose (3g/kg) load b. 30 minutes after glucose (3g/kg) load

Figure 7:
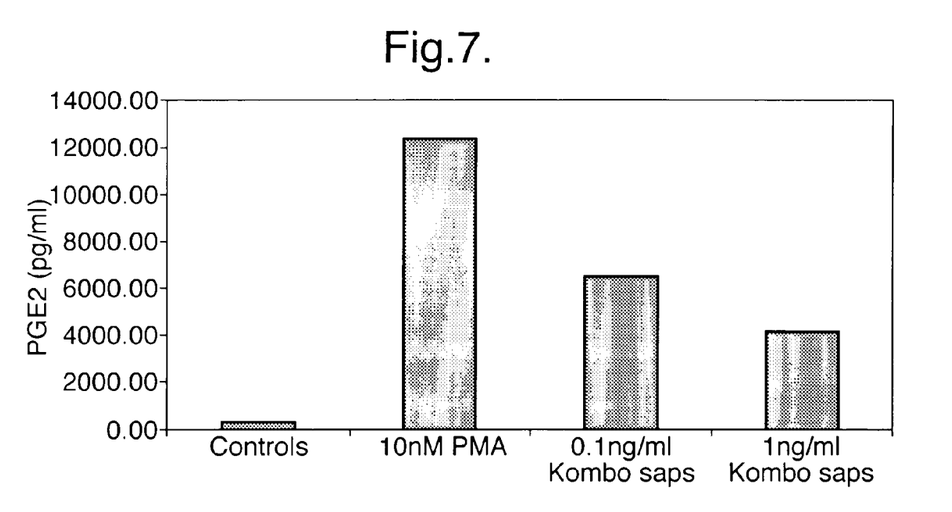
Figure 7A:
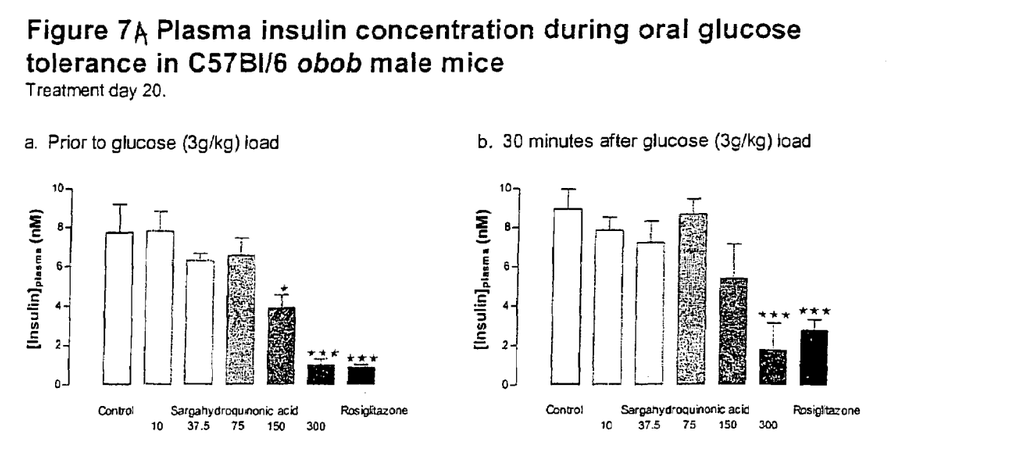

Figure 7A Plasma insulin concentration during oral glucose tolerance in C57Bl/6 *obob* male mice
Treatment day 20.

a. Prior to glucose (3g/kg) load b. 30 minutes after glucose (3g/kg) load

Fig.7.

FOOD SUPPLEMENTS COMPRISING, AS A HEALTH COMPONENT, SARGAHYDROQUINOIC ACID OR DERIVATIVE THEREOF

Kombo nut seed fat is a known product that can be obtained from the seeds of Pycnanthus angolensis (cf WO 96/39130) The components present in this fat were analysed by different groups and a number of terpenoid acid type ingredients were identified. One of these ingredients was identified as a novel polyprenylated hydroquinone substituted carboxylic acid named kombic acid which was identified as having a structure mentioned in Lok c.s. Phytochemistry 22, p. 1973 from 1983. (i.e. 16-($2^1$, $5^1$-dihydroxy-$3^1$ methylphenyl)-2,6,10,14 tetramethyl-2,6,10,14 hexadecatetraenoic acid). Although kombo nut oil, containing its terpenoid acid type ingredient is disclosed as useful and having a number of health benefits such as hypoglycemic activity, activity against fungal skin infections; activity for the treatment of shingles; or against leprosy; headaches, body aches; chest pains; or as an anti sterility agent for women; or as an antihelmintic; or poison antidote; or as an anti toothache agent; or as an anti bleeding agent; etc (cf WO 96/39130) no relation is given between the presence of a specific component and the occurrence of a specific health effect.

U.S. Pat. No. 3,615,588 discloses blends made from oils, rich in trimyristin and other oils. The trimyristin used can be obtained from Kombo nut oil.

We analysed the kombo nut fat further and found that this fat contains an ingredient which was identified by mass spectroscopy and $^{13}$C-NMR as sargahydroquinoic acid (=SHQA) [(CA name: 12-($2^1$,$5^1$-dihydroxy-$3^1$-methylphenyl)-6,10 dimethyl-2-($4^1$-methyl-$3^1$-pentenyl)-2E, 6E, 10E dodecatrienoic acid)] and that this compound and a number of its derivatives displays useful health benefits. This compound SHQA is normally applied in combination with glycerides. These glycerides can be the triglycerides present in kombo nut oil but also other glycerides can be used in combination with SHQA.

Therefore our invention in the first instance concerns blends comprising a substituted organic acid, or a derivative thereof and a glyceride wherein the blends comprise (i) 0.1 to 99.9 wt %, preferably 2 to 95 wt % more preferably 10 to 80 wt % of a hydroquinone substituted poly unsaturated fatty acid as present in kombo nut oil, in particular being sargahydroquinoic acid (=SHQA) or a derivative thereof, such as esters of these fatty acids with alcohols with 1 to 32 carbon atoms, or food acceptable salts thereof (ii) 0 to 99.8 wt %, preferably 4 to 97 wt %, more preferably 10 to 80 wt % of kombo butter glycerides and (iii) 0.1 to 99.9 wt %, preferably 1 to 94 wt %, more preferably 10 to 80 wt % of other triglycerides The derivatives of the substituted fatty acid preferably are selected from esters of the hydroquinone substituted polyunsaturated fatty acid and a straight chain saturated and/or unsaturated alcohol with 2 to 20 carbon atoms, preferably with 14 to 18 carbon atoms. Other preferred derivatives are the Na or K or Ca salts of the hydroquinone substituted poly unsaturated fatty acid These products are easily made from the free acid by esterification with the required alcohol under well known conditions respectively by neutralisation of the acids with the required base.

It is also possible to use esters made from the hydroquinone substituted poly unsaturated fatty acid and a fatty acid with 2 to 32 carbon atoms by esterifying at least one of the hydroxy groups of the substituted acid.

The other glycerides can be selected from or derived from a wide range of natural glycerides e.g. the triglycerides selected from the group consisting of palm oil; cocoa butter; coconut oil; palm kernel oil; soy bean oil, olive oil; sunflower oil; rape seed oil; safflower oil; corn oil; cotton seed oil; cocoa butter equivalents or cocoa butter replacers; fish oil; borage oil, pine nut oil; coriander oil; fungal oils, or high oleic varieties thereof, or fractions thereof, or hardened varieties thereof, or fractions of the hardened varieties or mixtures of one or more of these oils and fats.

For foods it is however preferred to use a triglyceride that provides a blend with a suitable unstabilised N-value as measured by NMR pulse techniques, because this will make the application of these blends in food products far easier. Unstabilised meaning that the N-value is measured after first melting the blend above 80° C., whereupon the melt is cooled to 0° C. and kept at 0° C. for 30 min, then the blend is heated to measurement temperature and kept at that temperature for 30 min, whereupon the N-value is measured. Preferred N-values for the blend are an $N_5$=5 to 80, preferably 10 to 70 and $N_{35}$=less than 20, preferably 1 to 5.

Instead of blending the substituted acid with glycerides we also can blend them with free fatty acids such as conjugated linoleic acid (=CLA), linoleic acid (both alpha and gamma), fish oils fatty acids, or other poly unsaturated fatty acids such as punicic acid, eleostearic acid, parinaric acid etc Although the hydroquinone substituted poly unsaturated fatty acid component can be obtained along different routes including synthetic routes starting from suitable materials it is preferred to isolate these components from natural sources. A preferred natural source that contains this acid in substantial amounts is the oil from the nuts of Pycnanthus angolensis. Another natural source is brown algae.(Chemistry Letters 1987, 1365-1366)

As the acids according to the invention are poly unsaturated these acids will be subject to deterioration due to oxidation. Therefore it is advisable to use these acids in combination with an anti oxidant. Suitable anti-oxidants can be selected from the group consisting of natural or synthetic tocopherols, butylated hydroxy toluene (BHT), tert-butylhydroquinone (TBHQ) butylated hydroxy anisole (BHA). propylgallate; free radical scavengers, enzymes with anti oxidant properties and ascorbyl esters of fatty acids. The amounts wherein the anti-oxidants are applied can be indicated as effective amounts, the actual amount will depend on factors like type of anti-oxidant, type of poly unsaturated acid present; type of food; presence of other components etc. However the effective amount for each specific situation can easily be determined by the man skilled in the art.

According to another embodiment of our invention our invention also concerns food products that comprise an effective amount of a health component wherein the health component is a hydroquinone substituted poly unsaturated fatty acid as present in kombo nut oil or extracts thereof or a derivative thereof, in particular being sargahydroquinoic acid (=SHQA) or a derivative thereof. The substituted acid preferably being the acid as obtained from kombo nut oil.

In principle the food product can be any food product that can be combined with the substituted acids or their derivatives. However we prefer to use this component in food products selected from the group consisting of margarine; fat continuous or water continuous or bicontinuous spreads, fat reduced spreads; confectionery products such as chocolate or chocolate coatings or chocolate fillings or bakery fillings, ice creams, ice cream coatings, ice cream inclusions, dressings, mayonnaises, cheese, cream alternatives, dry soupes, drinks, cereal bars, sauces, bakery products and snack bars.

Instead of using the substituted acids in food products we can also use them in food supplements. Therefore part of our invention are also food supplements comprising an effective amount of a hydroquinone substituted poly unsaturated fatty acid, as present in kombo nut oil or extracts or a derivative thereof in particular being sargahydroquinoic acid (=SHQA) or a derivative thereof in an encapsulating material or in granules or in powder form. The encapsulating material for the supplements is preferably selected from the group consisting of gelatin; starch, modified starch, flour, modified flour, sugars, in particular sucrose, lactose, glucose and fructose.

We found that our newly identified acid components have a number of useful health benefits. Therefore our invention also concerns the use of a composition comprising a hydroquinone substituted poly unsaturated fatty acid as present in kombo nut oil or extracts thereof or a derivative thereof as an active ingredient for the preparation of food compositions or food supplements with a health effect, wherein the health effects include acting as a lipase inhibitor, in particular as an inhibitor for pancreatic lipase or gastric lipase and/or acting as a ligand for peroxisome proliferator activated receptors subtype alpha or gamma and/or reducing and/or preventing ageing, in particular ageing of the skin and/or acting on photo damaged skin; and/or promoting the formation of decorin in the dermis of the skin and/or treating/preventing acne and/or treating/preventing cellulite and/or enhancing body or oral freshness. Alternatively the compositions can also be applied in topical compositions for cosmetics.

Other health effects that we found are the following: the hydroquinone substituted poly unsaturated fatty acid have unexpected good anti oxidant activity which was even higher than for other well known anti oxidants such as tocopherols. This anti oxidant activity resulted in the delay of oxidation of fats and oils and could further be used to prevent or retard the development of diseases related to the presence of free radicals.

Therefore our invention also concerns the use of a hydroquinone substituted poly unsaturated fatty acid as present in kombo nut oil, in particular being sargahydroquinoic acid (=SHQA) or a derivative thereof, such as esters of fatty acids with 1 to 32 carbon atoms, or food acceptable salts thereof wherein the hydroquinone substituted poly unsaturated fatty acid or derivative thereof is used to prevent the formation of free radicals and/or to delay the oxidation of fats and oils and/or to help prevent or retard the development of diseases in mammals related to the presence of free radicals. In particular the SHQA or its derivatives is used to prevent or retard the development of cancer and/or of Alzheimer disease and/or of arthritis and/or of cardiovascular diseases.

Preferred derivatives that are used herefor are esters of the hydroquinone substituted poly unsaturated fatty acid and a straight chain saturated and/or unsaturated alcohol with 6 to 20 carbon atoms, preferably with 14 to 18 carbon atoms. Other preferred derivatives are the hydroquinone substituted poly unsaturated fatty acid salts of Na or K or Ca, because these derivatives dissolve better and moreover also provide minerals upon use.

Other preferred derivatives that can be applied are the esters of the hydroquinone substituted poly unsaturated fatty acid such as SHQA wherein the hydroxy group or groups of the hydroquinone substituted poly unsaturated fatty acid is (are) esterified with a straight chain saturated and/or unsaturated fatty acid with 6 to 20 carbon atoms.

Although the novel ingredients are very effective as anti oxidant we also found that synergies can be achieved by using mixtures thereof with other known anti oxidants. Therefore we prefer to apply a mix of our SHQA derivative with an effective amount of one or more other anti oxidants, preferably selected from the group consisting of natural or synthetic tocopherols, tocotrienols, BHT, TBHQ, BHA, propylgallate; free radical scavengers, enzymes with anti oxidant properties and ascorbyl esters of fatty acids.

We further found that these substituted acids also have beneficial acetylcholine esterase activity. Therefore these compounds also can be used in Alzheimer disease for enhancing cognitive function, myasthenia gravis, glaucoma and for enhancing learning and memory. Pancreatic lipase inhibitors such as Xenical (Orlistat) are known to decrease fat hydrolysis in the gastrointestinal tract and fat absorption reducing body weight in vivo. Therefore our compositions have the ability to prevent/reduce the accumulation of body fat and help to prevent/treat obesity. Furthermore the substituted acids will have effects on promoting leaness and have mild laxative effects.

Other health effects include the action of our substituted acids acting as a ligand for peroxisome proliferator activated receptors such as subtype alpha or gamma. These transcription factors are key regulators of both lipid and glucose metabolism and our substituted acids will help optimise these. Effects of our substituted acids which could be attributed to PPAR alpha will include improving lipid metabolism, control of hyperlipedimia and assisting in both the prevention and treatment of cancer.

Insulin is a hormone essential for maintaining blood glucose levels within normal and healthy limits. If insulin action is impaired, as found in the human condition of insulin resistance, this can lead to a number of health problems. Short term the types of problems associated with insulin resistance comprise cognitive impairment (poor memory), chronic fatigue (lack of energy) and mood swings. More long term, the onset of diseases such as cardiovascular disease, type-2 diabetes and polycystic ovary syndrome are common.

Peroxisome proliferator activated receptor gamma (PPAR gamma) is a nuclear hormone receptor which forms part of the PPAR group of transcription factors. These are ligand activated transcription factors which bind DNA in a heterodimeric complex with a second nuclear hormone receptor RXR. PPAR gamma is thought to play a role in the control of insulin sensitivity, blood sugar levels, along with other biological effects including inflammation, cancer, cognition and cellular differentiation. PPAR gamma is also known to be an important regulator of lipid metabolism. Because of its interaction with PPRA gamma our substituted fatty acids will display beneficial effects on insulin resistance and related disorders such as polycystic ovary syndrome, type-2 diabetes, gestanional diabetes, Syndrome X, hypertension, stroke, glucose metabolism. Effects will include reducing blood glucose levels and cognitive performance. The substituted acids also have anti inflammatory activities and activities for the prevention or treatment of cardiovascular diseases, joint diseases, arthritis, peptic ulcer disease, inflammatory bowel disease, inflammatory skin conditions, neurodegenerative diseases and allergies.

The skin anti ageing properties are very useful to boost the levels of dermal proteins collagen or decorin having benefits in reducing the wrinkling, sagging, lining of the skin. In addition benefits in reducing age spots, enhancing tissue repair, soothing of irritated, red or sensitive skin and improvement of texture, smoothness and firmness of the skin can be achieved by the use of our compositions. Further our novel compositions can also be used as flavouring agent to achieve a bitter taste e.g. inbiter drinks or in bittersweet chocolate.

As a last embodiment of our invention our invention also concerns a process for the enrichment of a hydroquinone substituted poly unsaturated fatty acid, in particular of SHQA, as present in kombo nut oil or derivatives thereof in a glyceride surrounding wherein:

(i) a kombo nut oil is selected containing a sufficient amount of the desired acid or acid derivative thereof (ii) the oil is refined by neutralization by adding a base at a temperature of 40 to 60° C., preferably 45 to 50° C.

(iii) the crude reaction product is separated in an organic phase and a water phase (iv) the water phase of step (iii) is acidified to a pH of 0 to 4, preferably 0.5 to 1.5 and the oily layer is drained off.

(v) a product is recovered that contains the hydroquinone substituted poly unsaturated fatty acid in amounts of more than 20 wt %

EXAMPLES

Example 1

Effects of Sargahydroquinoic Acid on Pancreatic Lipase

Lipase Inhibition Assay Methodology

This assay is developed from the colormetric Sigma assay (Lipase-PS™) for the quantitative kinetic determination of pancreatic lipase activity in serum at 550 nm.

Reactions: Serum pancreatic lipase catalyses the hydrolysis of a natural 1,2-Diglyceride to form monoglyceride and fatty acid. The monoglyceride is hydrolysed by monoglyceride lipase (MGLP) to form glycerol and fatty acid. Glycerol is then phosphorylated by glycerol kinase (GK) in the presence of ATP to form glycerol-3-phosphate which is oxidised by glycerol-3-phosphate oxidase (GPO) to form dihydroxyacetone phosphate (DAP) and hydrogen peroxide ($H_2O_2$). Subsequently $H_2O_2$ reacts with 4-aminoantipyrine (4-AAP) and sodium N-ethyl-N-(2-hydroxy-3-sulfopropyl)-m-toluide (TOOS) in the presence of peroxidase (POD) to form a quinone diimine dye. The dye absorbs light at 550 nm. The rate of increase in absorbance at 550 nm is directly proportional to the pancreatic lipase activity in the sample.

Figure 1:
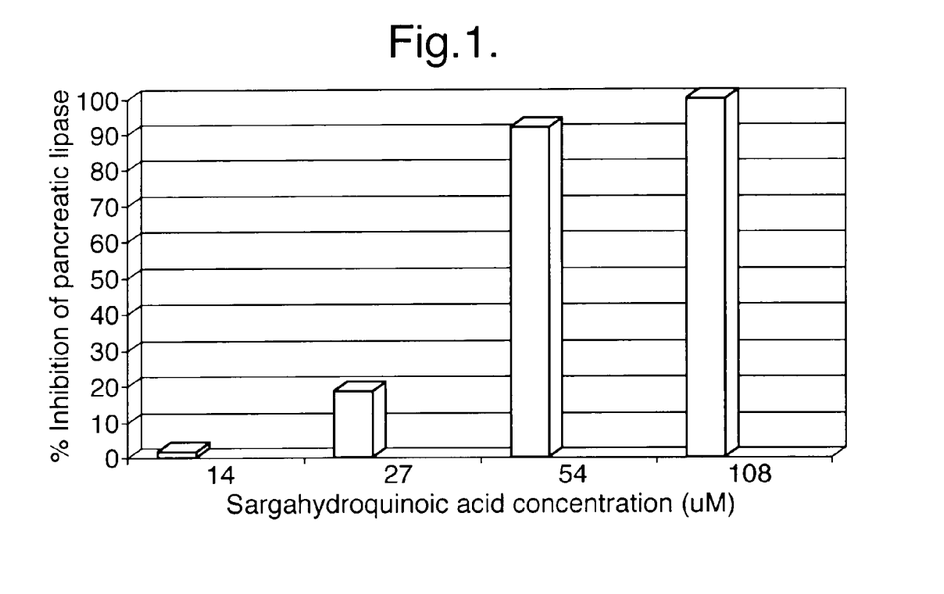

Reagents:

The Sigma diagnostics lipase-PS Reagents, are reconstituted according to the instructions. Substrate solution reagent (145 µl), along with either 5 µl of water (blank wells) or lipase-PS standard, and 20 µl blank solvent (ethanol/THF/acetone; 60:20:20) or samples in solvent (Sargahydroquinoic acid) in triplicate are added to each of the wells. Plates are incubated at room temperature for 8 minutes with agitation. Lipase-PS activator (50 µl) is added to all wells and absorbance at 550 nm measured kinetically on the microtitre reader for 0-30 minutes, with readings every 60 seconds and shaking before each reading. The slope of the readings in the 6-24 minute linear range is calculated, minus the average slope of the blanks. Results are expressed as mOD/min, less than or greater than the +ve control. Final results expressed as % inhibition of the control sample, are illustrated by FIG. 1.

Example 2

Antiageing Effects

Procedure for Measuring Procollagen-I and Decorin Synthesis In Human Dermal Fibroblasts Preparation of Dermal Fibroblast Conditioned Medium Primary human foreskin fibroblasts at passage 2 (P2) were seeded into 12-well plates at 10000 cells/cm² and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagents (retinoic acid or Sargahydroquinoic acid) and vehicle controls (in DMSO) were added to the cells in triplicate in a final volume of 0.4 ml/well fresh serum free DMEM and incubated for a further 24 hours. This fibroblast conditioned medium was either analysed immediately or snap frozen in liquid nitrogen and stored at −70° C. for future analysis. The cells were then counted and data from the dot-blot analysis subsequently standardised to cell number.

Dot Blot Assay for Procollagen-I and Decorin Protein in Dermal Fibroblast Conditioned Medium Samples of conditioned medium from dermal fibroblasts treated with vehicle (as a control) or test reagents were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes. A standard for the assay was generated by serial dilution of neat fibroblast conditioned medium from fibroblasts seeded at 10000 cells/cm² in a 175 cm² flask and maintained in serum free DMEM as described above.

Assay samples were subsequently applied in triplicate to a pre-wetted sheet of Immobilon-P transfer membrane using the 96-well Bio-Dot Apparatus from Bio-Rad as described in the manufacturers' guidelines. Approximately 200 µl of medium was applied per well. The medium was allowed to filter through the membrane under gravity (30 minutes) after which the membrane was washed twice with PBS (200 µl). These PBS washes were allowed to filter through the membrane under gravity (2×15 minutes). The Bio-Dot apparatus was then attached to a vacuum manifold and a third and final PBS wash carried out under suction. The apparatus was disassembled, the membrane removed and quickly cut as required before being placed in blocking buffer overnight at 4° C.

Membranes prepared for decorin analysis were blocked with 3% (w/v) BSA/0.1% (v/v) Tween 20 in PBS The following day, the membranes were probed with 1:10000 dilution of primary antibodies to human decorin (rabbit polyclonal Biogenisis) for 2 hours at room temperature. The membranes were subsequently washed with TBS/0.05% Tween 20 (3×5 minutes) and then incubated with 1:1000 dilution of $^{125}$I-conjugated anti-rat or anti-rabbit F(ab')2 fragments (Amersham) as required for 1 hour at room temperature.

Figure 2:
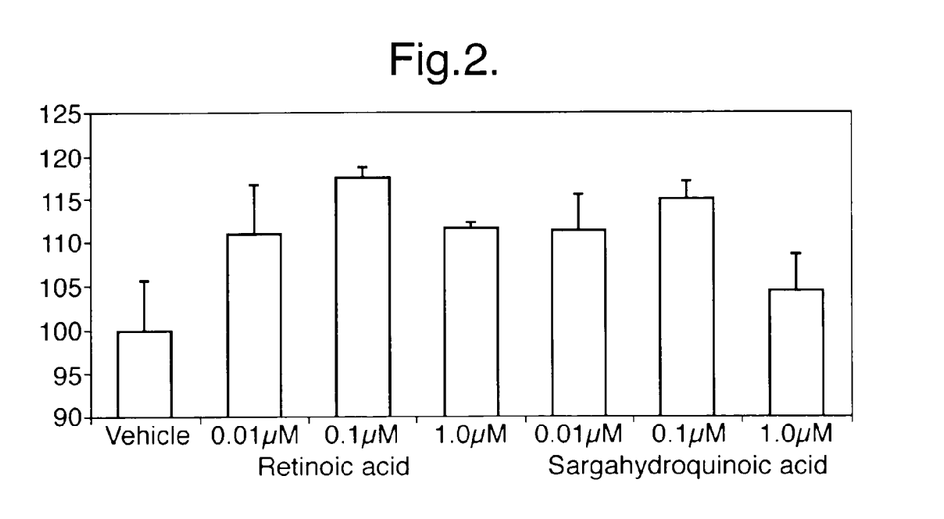

Following this the Immobilon strips were again washed with TBS/Tween 20 (3×5 minutes) before being allowed to dry in air at room temperature. The dried membranes were wrapped in cellophane and exposed to a Molecular Dynamics storage phosphor screen for 16-18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardised to cell number and the effects of actives such as SHQA on decorin synthesis were determined relative to a vehicle treated control value of 100 arbitrary units. A comparison of the effects of retinoic acid vs Sargahydroquinoic acid are shown in FIG. 2.

The level of decorin in skin is associated with improved condition and appearance of skin. Increasing the level of decorin in skin is important for controlled and correct deposition of collagen in skin which is associated with many skin benefits such as wrinkle effacement and dermal repair of photodamaged skin. Sargahydroquinoic acid enhances decorin production and this effect is similar to that observed for retinoic acid.

Example 3

Effects of Sargahydroquinoic Acid on PPARα (reporter gene assay)

Cell Culture and Reporter Gene Assay

Cos-7 cells (ECACC No. 87021302) were routinely grown in DMEM with 10% FCS (foetal calf serum) at 37° C., 5% $CO_2$ to 80% confluency. Transient transfections were performed as described by the manufacturers (GibcoBRL). Briefly, cells were plated out in 24 well plates at 50,000 cells per well and incubated overnight in DMEM with 10% FCS at 37° C., 5% $CO_2$. Cells were then transfected using the LipofectAMINE reagent. For each well, 0.5 µg of DNA mix (for "control" cells pPPRE$_3$TK-luc 0.40 µg; pRL-TK 0.04 µg; pcDNA3.1(−) 0.03 µg; pRSV 0.03 µg; for "plus RXR" cells pPPRE$_3$TK-luc 0.40 µg; pRL-TK 0.04 αg; pcDNA3.1(−) 0.03 µg; pRSV/RXRα 0.03 µg; for "plus PPARα" cells pPPRE$_3$TK-luc 0.40 µg; pRL-TK 0.04 µg; pcDNA3.1(−)/PPARα 0.03 µg; pRSV 0.03 µg) in 25 µl of DMEM was incubated with 1 µl LipofectAMINE, and also in 25 µl of DMEM for 45 minutes. The mixture was then made up to 250 µl per well and added to the cells, which had been washed with 1 ml of DMEM. Cells were then incubated for 5 hours at 37° C., 5% $CO_2$ and 250 µl DMEM with 20% SBCS (charcoal stripped bovine calf serum; Sigma) added. Cells were allowed to recover for 18 hours at 37° C., 5% $CO_2$ before being treated. The transfection mix was removed from the cells and replaced with treatment mix (DMSO or 10 µM Sargahydroquinoic acid) and incubated for 24 hours at 37° C., 5% $CO_2$. Sargahydroquinoic acid was made up as 10 mM stock in DMSO and diluted 1000-fold into DMEM containing 10% SBCS (500 µl per well) immediately before being added to the cells. Each treatment was performed in triplicate. Cells were then washed with 1 ml of PBS (without calcium or magnesium) and lysed with 100 µl per well of 1×Passive Lysis Buffer (as supplied with Promega Dual Luciferase assay kit). Lysis was allowed to continue for 15 minutes and then the lysate was assayed for Firefly and Renilla luciferase activity using the Promega Dual Luciferase assay kit. For the assay 20 µl of lysate was taken and assayed as described in the kit instructions using a MLX microtiter plate luminometer (Dynex).

Figure 3:
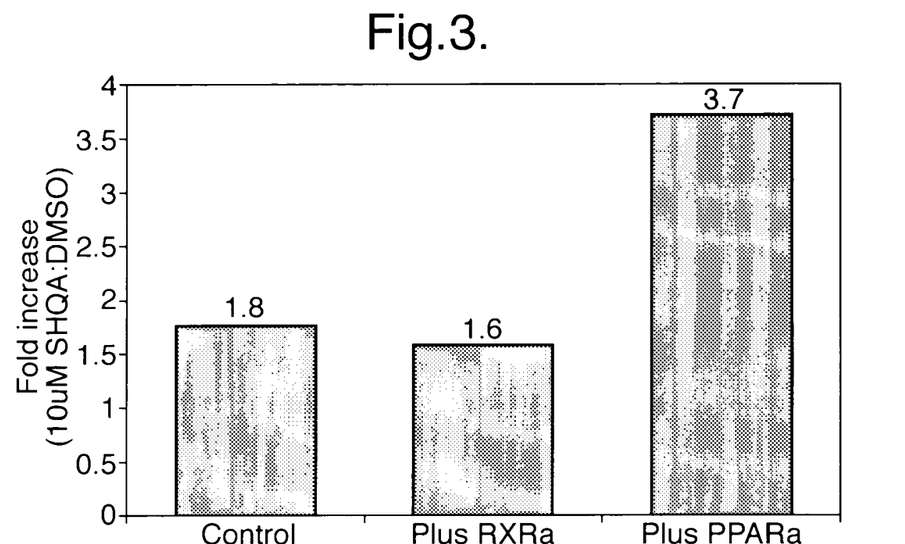

As shown in FIG. 3 SHQA is a PPAR alpha rather than an RXR ligand. Health effects associated with PPAR alpha activation will include optimising lipid metabolism, prevention and treatment of cancer, anti-inflammatory effects.

Example 4

Effects of Sargahydroquinoic Acid on PPARγ (reporter gene assay)

Reporter Gene Assay

This assay is based on that described by Kliewer et al (Nature 358 771-774 1992). In brief, cos-7 cells (ECACC No. 87021302) were seeded in 24-well plates at a density of 0.325×10$^5$ cells/well. Cells were grown overnight at 37° C./5% $CO_2$ in DMEM containing 10% FCS, 2 mM L-glutamine, 100 iu/ml penicillin and 100 g/ml streptomycin. Cells were washed with transfection media (DMEM containing 2 mM L-glutamine) then transiently transfected with 4 plasmids: a PPAR-responsive firefly luciferase reporter gene (pPPRE3TK-luc); mammalian expression plasmids (pcDNA3/hPPARγ1 and pRSV/hRXRα) containing human PPARγ1 and RXRα cDNAs respectively and a control plasmid (pRLTK, Promega) which constitutatively expresses the renilla luciferase gene. Transfection was performed using Lipofectamine (Gibco Brl) as directed by the manufacturers. Transfected cells were incubated for 6 h at 37° C./5% $CO_2$ and then for a further 46 hours in the presence or absence of ligand. After 46 hours cell lysates were prepared and the level of firefly and renilla luciferase determined using the Dual luciferase assay system (Promega) and a MLX microtitre plate luminometer (Dynex). The level of firefly luciferase (normalised against the renilla luciferase control) provides a measure of reporter gene activity. This in turn reflects the level of PPARγ activation.

Figure 4:
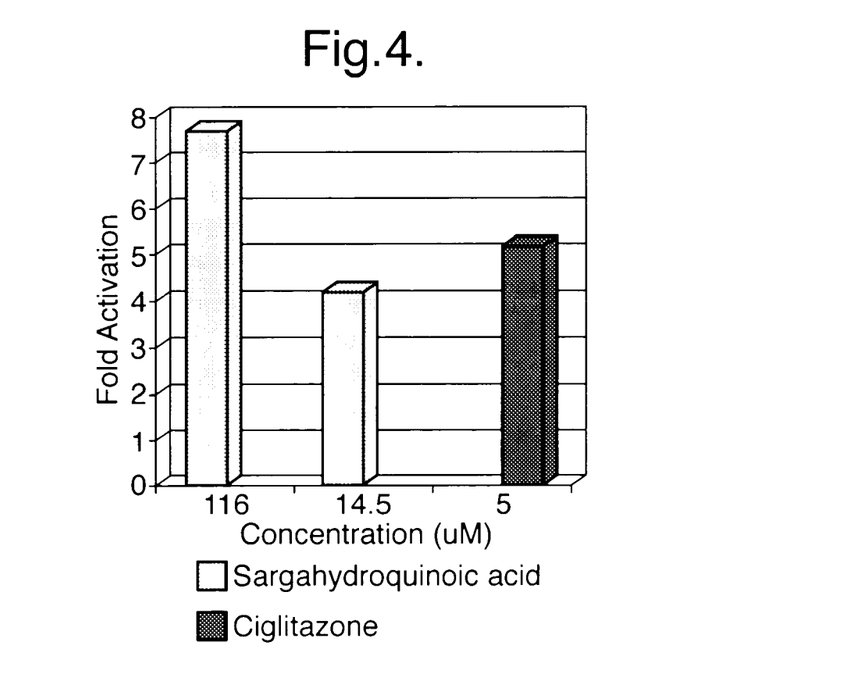

FIG. 4 illustrates that Sargahydroquinoic acid gives good activation of PPARγ. SHQA will have benefits in a range of conditions, including in the short term, chronic fatigue, cognitive impairment (memory) and mood swings. Long term benefits would be focused on cardiovascular disease (lipid lowering), type-2 diabetes (common in older age) and polycystic ovary syndrome.

Example 5

Effects of Sargahydroquinoic Acid on Microbial Number and Biotranformations

The reduction in microflora on the body or within the mouth and inhibition of the biotransformation of fatty acids to volatile fatty acids has benefits in the reduction of body or oral malodour.

In Vitro Evaluation of Sargahydroquinoic as a Deodorant Active

The in vitro model system, reproducing fatty acid catabolism by Ceorynebacteria A, consisted of 250 ml baffled shake flasks, to which were added 30 ml semi-synthetic medium (see below) supplemented with fatty acid substrate (2.0 mg/ml pentadecanoic acid) and non-fatty acid substrate (0.5 mg/ml glucose). This system was employed to evaluate sargahydroquinoic acid as a potential deodorant active; to each flask (other than the control) was added a specific dose of sargahydroquinoic acid, from a 25 g/l stock emulsion in semi-synthetic medium supplemented with 5.0 mg/ml Gum Arabic (formed by ultra-homogenisation at 24000 rpm for 1 min). Flasks were inoculated with fresh bacterial biomass (Corynebacterium A NCIMB 40928), pre-grown for 24 h in TSBT (see below), to give starting optical densities ($A_{590}$) of ~1.0. Following inoculation, flasks were incubated aerobically at 35° C., with agitation (130 rpm), and analysed after 24 h. Culture viability was determined by total viable count (TVC) analysis on TSAT plates (see below) following serial dilution in quarter-strength Ringers solution. Fatty acid concentrations were determined by capillary gas chromatography (GC) (see below), while residual glucose levels were measured with blood glucose test strips (BM-Test 1-44; Boehringer Mannheim) used in conjunction with a RefloftuxS glucose meter (Boehringer Mannheim). A 'sub-lethal' effect is defined as significant inhibition of fatty acid catabolism, typically greater than 50% inhibition of pentadecanoic acid utilisation, without concomitant reductions in Corynebacterium A viability ($\leq 1$ log$_{10}$ CFU/ml reduction) or glucose utilisation ($\leq$10% reduction). Outside one or both of these defined boundaries, the effect may be described as 'antimicrobial', where 'antimicrobial' includes both bacteriostatic & bactericidal effects.

Composition of Tween-supplemented Tryptone soya broth & agar (TSBT & TSAT) used for growth & maintenance of axillary bacteria (g/l): Tryptone soya broth (30.0); Yeast Extract (Beta Lab) (10.0); Tween 80™ (1.0); ±Agar (20.0). Composition of semi-synthetic medium used in in vitro system simulating fatty acid catabolism by corynebacteria A (g/l): $KH_2PO_4$ (1.6); $(NH_4)_2HPO_4$ (5.0); $Na_2SO_4$ (0.38); Yeast Nitrogen Base (Difco) (3.35); Yeast Extract (Beta Lab) (0.5); Tween 80™ (0.2); Triton X-100™ (0.2); $MgCl_2.6H_2O$ (0.5).

Fatty acid levels in the flasks were determined by capillary GC analysis. Initially, 5.0 ml aliquots from each flask were transferred into universal tubes; an internal standard (lauric acid, 1.0 mg/ml final concentration) was added to each tube and the culture medium acidified (pH ~2) by the addition of hydrochloric acid. Liquid-liquid extraction was then carried out using 2 vol (10 ml) ethyl acetate; organic and aqueous phases were resolved by centrifugation (2000 rpm, 3 min). ~0.75 ml of each organic (upper) phase was then transferred to a sampling vial prior to analysis on a Perkin Elmer 8000 (Series 2) GC fitted with a 15 m×0.32 mm (internal diameter) FFAP (nitroterephalic acid modified PEG/siloxane copolymer) fused silica capillary column (film thickness 0.25 mm) (Quadrex). This column was attached to the split-splitless injector and flame ionisation detector (FID) of the GC; injector and detector temperatures were each 300° C. Carrier gas for the column was helium (6 psi), while hydrogen (17 psi) and air (23 psi) supplied the FID. The temperature programme for fatty acid analysis was 80° C. (2 min); 80-250° C. (20° C./min); 250° C. (5 min). Sample size for injection was 0.5-1.0 µl. Fatty acid levels in the flasks were quantified by comparison of peak areas with known levels of both internal (lauric acid) and externally-run (pentadecanoic acid) standards.

Results

| [Sargahydro-quinoic acid] (g/l) | TVC ($\log_{10}$ CFU/ml) | Glucose Utilisation (%) | Pentadecanoic Acid Utilisation (%) | Inhibition of Utilisation (%) |
|---|---|---|---|---|
| 0.0 | 8.40 | 100 | 100 | 0 |
| 0.05 | 8.67 | 100 | 99 | (1) |
| 0.1 | 8.83 | 100 | 58 | 42 |
| 0.25 | 7.93 | >90 | 15 | 85 |
| 0.5 | 7.85 | 100 | 19 | 81 |
| 1.0 | 7.3 | >90 | 5 | 95 |
| 2.5 | <3.0 | 7 | 25 | 75 |

Effects in bold denote sub-lethal inhibition of pentadecanoic acid utilisation; other effects are due to antimicrobial (bacteriostatic or bactericidal) inhibition or, where in parentheses, are not significant.

Example 6

Antioxidant Activity of Sargahydroquinoic Acid (SHQA) Containing Extract from Kombo Nuts Method of Analysis: Rancimat All oils and fats have a resistance to oxidation which depends on the degree of saturation, natural or added antioxidants and prooxidants. Oxidation is slow until this resistance is overcome, at which point oxidation accelerates and becomes very rapid. The length of time before this rapid acceleration of oxidation is the measure of the resistance to oxidation and is commonly referred to as the "induction period".

Method for the determination of the oxidative stability of animal and vegetable oils and fats.

The method describes the determination of the oxidative stability of an oil or fat by means of the Swift Induction period test. A flow of purified air is led through the sample that is heated between 90° C. and 140° C. The released gasses formed by oxidation are led by an air flow through a measurement vessel with water. The conductivity of the water is measured by Metrohm rancimat and registered. An increase of the conductivity due to degradation components means the end of the induction period. The Swift Induction period is measured in hours.

Reagents and Equipment
acetone
molecular sieve
petrol ether
Metrohm rancimat 743
legally stamped thermometer Sample Preparation To sunflower oil different concentrations of tocomix and SHQA containing extract were added (see table). Sample size: ~3 g Sample Storage Between preparation and measurement of the rancimat, the sample must be closed immediately using plugs made of glass or cork and stored in the refrigerator. The Rancimat is measured as soon as possible.

| | Sunflower oil | Tocomix (50% tocopherol) | ~56% SHQA containing extract | Swift induction period |
|---|---|---|---|---|
| Sample 1 (Reference) | 100% | | | 3 hours |
| Sample 2 | 99.975% | 0.025% | | 3 hours |
| Sample 3 | 99.95% | 0.05% | | 3 hours |
| Sample 4 | 99.8% | 0.2% | | 4 hours |
| Sample 5 | 99.5% | 0.5 | | 4 hours |
| Sample 6 | 99.975% | | 0.025% | 4 hours |
| Sample 7 | 99.95% | | 0.05% | 6 hours |
| Sample 8 | 99.8% | | 0.2% | 12 hours |
| Sample 9 | 99.5% | | 0.5 | 17 hours |

Conclusion

In all cases for the sunflower oil containing SHQA extract a longer swift induction period was measured as compared with sunflower oil containing tocomix. Therefor for the SHQA containing extract a higher antioxidant activity then for tocomix has been demonstrated.

Example 7

Sargahydroguinoic Acid (SHQA) as a Cholesterol Esterase Inhibitor

Methodology

All assay materials were obtained from Sigma, except cholesterol esterase which was obtained from Biozyme Laboratories Ltd. Sargahydroquinoic acid (SHQA, ~90% purity) was obtained by hexane extraction of kombo nuts, followed by silica chromatography.

Preparation of Fat Phase

Cholesterol, oleic acid and SHQA were weighed into an 8 mL vial with enough diethyl ether to dissolve the mixture (0.018 g cholesterol, between 0.009 g and 0.036 g of SHQA and 0.09 g oleic acid in 6 mls of diethyl ether). The ether was evaporated to dryness using a stream of dry nitrogen.

Preparation of Assay Buffer

Sodium taurocholate, bovine serum albumin and ammonium chloride were dissolved in a 0.154 mM phosphate buffer at pH6.2 (typically 0.52 g sodium taurocholate, 0.23 g bovine serum albumin and 0.18 g ammonium chloride were dissolved in 50 mls of buffer)

Preparation of Esterase Solution

Cholesterol esterase (ex Biozyme, source pig pancreas) was dissolved in 0.154M phosphate buffer at pH6.2.

Assay Method.

Assay buffer (6 mls) was added to the dried lipid mixture mixed using a whirlimixer then placed in an ultrasonic bath at 60° C. for 30 minutes. The vials were sealed and transferred to a shaking water bath (200 shake/min) at 37° C. for 15 minutes. 6 mls of esterase solution were added and the vials resealed and shaken at 37° C. 1 ml samples were taken, immediately after addition of the esterase and after shaking for 1 hour, which were added to 3 mls of isopropanol and heated at 80° C. for 30 minutes to destroy esterase activity and to precipitate protein material. The samples were acidified with concentrated hydrochloric acid, 4 mls of water added and the lipids extracted with two aliquots of warm diethyl ether then dried with sodium sulphate. The diethyl ether was removed and the extracted lipids silylated by heating with 200 µl bis (trimethylsilyl) tri flluoroacetamide (BSFTA) and 100 µl pyridine for 30 minutes, then analysed by carbon number GC.

As shown in FIG. 5, the presence of SHQA inhibited the conversion of cholesterol to cholesterol oleate. This reflects an inhibition of cholesterol esterase.

Effect of the Addition of SHQA on the Activity of Acetylcholine Esterase

Acetylcholine esterase activity was measured using 96-well mircoplate reader based on Ellmans method (G. I Ellman, D. Courtney, V. Andres Jr., R. M. Featherstone Biochem. Pharmacol.7 (1961) 88.

The SHQA (purified by silica chromatograph) was dissolved in a mixture of ethanol/tetrahydofuran/acetone 60/20/20 at a concentration of 100 mg/ml. Serial dilutions were then made as required. These solutions were further diluted 1 in 10 using 50 mM Tris-HCL buffer pH 8.

SHQA solutions (20 µl), acetylthiocholine iodide (ACTI; 25 µl 15 mM in water), dithiobisnitrobenzoic acid (DNTB; 125 µl 3 mM in 50 mM Tris-HCL buffer pH 8 containing 0.1M NaCl and 0.02M $MgCl_2.6H_2O$), Tris-HCL buffer (50 µl; 50 mM pH 8 containing 0.1% bovine serum albumin) were placed in wells together with acetyl choline esterase from electric eel (Sigma type VI-s lyophilised powder) (20 µl 1.5 µg/ml in 50 mM Tris-HCL pH 8 buffer containing 0.1% bovine serum albumin)

The absorbance was measured at 410 nm every 13 s for 8 times. The rate of change of OD of the test materials was compared to the blank solutions.

As shown in FIG. 6, SHQA was shown to inhibit acetylcholinesterase activity.

Example 8

The Anti-inflammatory Effects of Kombo Nut Oil

The anti-inflammatory effects were determined by in vitro tests wherein the production of Prostaglandin E2 (=PGE2) production by the human skin fibroblasts is measured after being induced by the inflammatory modulus Phorbol myristate acetate (PMA). A reduction in the levels of PGE2 is indicative for the anti-inflammatory effect.

Primary human foreskin fibroblasts at passage 2 (P2) were seeded into 96-well plates at 10000 cells/well and maintained for 24 hours in an atmosphere of 5% carbon dioxide in Dulbeccos Modified Eagles Medium (DMEM) supplemented with 10% foetal calf serum. Kombo nut oil saponifiables (containing SHQA) were added to fresh cell media in ethanol (final concentration 1%) in triplicate and incubated for a further 24 hours. PMA in ethanol/cell media was added to the media and the cells incubated for a further 24 hours. PMA represents an external stressor which induces oxidative stress and inflammatory responses in cells. The fibroblasts/media were then analysed as described below immediately or snap frozen in liquid nitrogen and stored at −70° C. for future analysis.

Prostaglandin E2 (PGE2) assay Volumes of 50 µl culture medium were taken for PGE2 assay after gently shaking the culture plate. PGE2 levels in the medium were determined with a Biotrak PGE2 immunoassay kit (Amersham, UK). The assay is based on the competition between unlabelled PGE2 in the sample and a fixed quantity of horseradish peroxidase labelled PGE2 for a limited amount of fixed PGE2 specific antibody. Concentrations of unlabelled sample PGE2 are determined according to a standard curve which was obtained at the same time.

The effects of Kombo nut oil saponifiables on PGE2 levels is shown in FIG. 7.

The graph (FIG. 7) demonstrates that challenging fibroblast cells with an inflammatory stimulus such as PMA causes an increase in the inflammatory response as measured by PGE2 production. Kombo nut oil saponifiables (saps), which contain sargahydroquinoic acid, even at the levels of 0.1 ng/ml, dramatically reduces the inflammatory response as measured by PGE2 production.—good anti-inflammatory activity.

Example 9

On Food Applications

Material and Methods

Production of SHQA
  The production of SHQA was carried out as follows:
  Deshelling of Kombo nuts
  Pressing of the deshelled Kombo nuts to extract the oil
  Filtration of the oil
  Neutralisation of the filtered oil to obtain SHQA-salts
  Recovery of SHQA by acidification
  The purity of the SHQA was approximately 75%. The remaining 25% consisted primarily of glycerides, ffa, and water.

Panelling
  Food products enriched with SHQA were compared to those made with a reference wherein SHQA was absent

A: Muesli Bars

Preparation of the Binding Mixture

| Ingredient | Percentage (SHQA-recipe) | Percentage (Reference-recipe) |
| --- | --- | --- |
| Bean oil | 40.8% | 43.0% |
| SHQA | 2.2% | 0.0% |
| Skimmed milk powder | 8.0% | 8.0% |
| Sugar | 49.0% | 49.0% |
| Lecithin | 0.4% | 0.4% |
| Cream vanillin | 0.03% | 0.03% |

Approximately 89% of the fat was mixed with the skimmed milk powder, the crystal sugar, the cream vanillin, and the lecithin for 40 min in a ball mill. The SHQA was homogeneously mixed by stirring with the remaining fat and then added to the binding mix. A binding mix without SHQA was used as reference.

Preparation of the Muesli Bars

Bars were made by mixing 55% of the binding mixture with 25% of the muesli mixture (supermarket type), 10% biscuit rework, and 10% of rice crisps. The mixture was then pressed in the moulds, cooled, de-moulded, coated, and cooled.

The following attributes were evaluated:
Crunchiness of the muesli bars
Overall appearance
Overall texture Conclusions From the results of the panelling the following conclusions could be drawn:
the overall texture, crunchiness and overall appearance of the bars were comparable in the bars containing the SHQA enriched binding mix and in the reference bars;
the addition of the SHQA to the binding mixture made the mixture slightly sticky, and therefore it had a minor negative effect on the de-moulding process. The higher stickiness did not, however, negatively effect the quality of the bars.

B: Preparation of the Bread

| Ingredient | Percentage (SHQA-recipe) | Percentage (Reference-recipe) |
| --- | --- | --- |
| Flour | 62.0% | 62.0% |
| SHQA-extract | 1.4% | 0.0% |
| Water | 33.0% | 33.0% |
| Yeast | 2.5% | 2.5% |
| Salt | 1.2% | 1.2% |

The yeast, previously dispersed in 85% of the water, was mixed with the flour and the salt. The SHQA extract and the remaining water were added and mixing was continued until a dough was formed.

After fermentation for 40 min and rework, carried out for three times, the bread was baked at 270° C. for 35 min. Bread without SHQA was used as reference.

Panelling
The following attributes were evaluated in bread:
Dough consistency
Structure
Overall appearance
Flavour
Softness and volume
Chewiness Conclusions From the results of the trial the following conclusions could be drawn:
The dough consistency, structure, softness, volume and chewiness were comparable in the SHQA enriched bread and in the reference bread.
Minor differences in the colour of the SHQA enriched bread were detected, nevertheless without affecting the quality of the bread.
The addition of the SHQA to the bread did not effect the characteristics of the dough during production and baking.

C: Coating for Muesli Bars

Preparation of the Coating

| Ingredient | Percentage (SHQA-recipe) | Percentage (Reference-recipe) |
| --- | --- | --- |
| Palm oil | 30.4% | 32.0% |
| SHQA | 1.6% | 0.0% |
| Skimmed milk powder | 10.0% | 10.0% |
| Sugar | 10.0% | 10.0% |
| Lecithin | 48.0% | 48.0% |
| Cream vanillin | 0.4% | 0.4% |

All ingredients except the fat, the SHQA and the lecithin were mixed in a Hobart mixer. As little as possible fat was added very slowly into the mix untill a dough was formed. The dough was then refined and conched, adding the remaining fat, except 6% of the total fat, into the conche. The lecithin was finally added 15 min before the end of the conching process. The SHQA was homogeneously mixed by stirring with the fat left and then added to the coating mix. A coating without SHQA was used as reference.

Preparation of the Muesli Bars

Muesli bars were coated and cooled in a cooling tunnel.

Panelling

Bars coated with the SHQA enriched coating were compared to the bars coated with a standard coating.

The following attributes were evaluated in the coating:
Overall appearance
Overall texture Conclusions From the results of the panelling the following conclusions could be drawn:
The addition of the SHQA to the coating mix did not effect the characteristics of the coating mix during the production and coating steps.
The overall texture of the SHQA enriched bars was comparable to that of the reference bars.
The colour of the coating of the SHQA enriched bars was slightly darker than that of the reference bars. Nevertheless the colour difference was not viewed as negative.

D: Ice Cream

Preparation of the Ice Cream

| Ingredient | Percentage (SHQA-recipe) | Percentage (Reference-recipe) |
| --- | --- | --- |
| Palm oil | 9.5% | 10.0% |
| SHQA-extract | 0.5% | 0.0% |
| Skimmed milk powder | 10.0% | 10.0% |

| Ingredient | Percentage (SHQA-recipe) | Percentage (Reference-recipe) |
|---|---|---|
| Crystal sugar | 12.0% | 12.0% |
| Clear syrup | 4.0% | 4.0% |
| Dextrose anhydrate | 2.0% | 2.0% |
| Dimodan PVP | 0.6% | 0.6% |
| Water | 61.4% | 61.4% |

The sugar, the milk powder and the dextrose were mixed and added to the water. The mixture was heated to 70° C. and the syrup was added. A fat/SHQA blend and the emulsifier were then added. The emulsion was stirred with an ultra-turrax, cooled down to 20° C. and stirred again with the ultra-turrax. The emulsion was left overnight in the refrigerator at 7° C. The emulsion was then stirred for 40 min in the ice cream machine, previously cooled down for 24 h at −20° C. The ice cream without SHQA was used as reference.

Panelling

The SHQA enriched ice cream was compared to the reference ice cream.

The following attributes were evaluated in the ice cream:
Overall appearance
Meltdown
Overall texture Conclusions From the results of the trial the following conclusions could be drawn:
The meltdown of the SHQA enriched ice cream was comparable to that of the reference ice cream.
Minor differences in the colour and texture of the SHQA enriched ice cream were detected if compared to the reference ice cream. Nevertheless such differences did not compromise the overall quality of the ice cream.
The addition of the SHQA to the ice cream did not effect the characteristics of the ice cream mix during processing.

E: Fat Based Spreads

Preparation of Fat Based Mint Spread

| Ingredient | Percentage (SHQA-recipe) | Percentage (Reference-recipe) |
|---|---|---|
| 96% bean oil/4% palm oil | 28.5% | 30.0% |
| SHQA | 1.5% | 0.0% |
| Full cream milk powder | 12.0% | 12.0% |
| Skimmed milk powder | 10.0% | 10.0% |
| Sugar | 48.0% | 48.0% |
| Lecithin | 0.4% | 0.4% |
| Cream vanillin | 0.03% | 0.03% |
| Mint flavour | 0.1% | 0.1% |
| Green colour | 1 drop | 1 drop |

Approximately 93% of the fat was mixed with the full cream milk powder, the skimmed milk powder, the crystal sugar, the cream vanillin, and the lecithin for 40 min in a ball mill. The SHQA was homogeneously mixed to the remaining fat by stirring and then added to the spread mix. A spread without SHQA was used as reference.

Panelling

The spread containing the SHQA was compared to the reference spread.

The following attributes were evaluated in the spread:
Overall texture
Overall appearance
Spreadability Conclusions From the results of the panelling the following conclusions could be drawn:
The overall texture, spreadability and overall appearance of the fat based mint spread enriched with SHQA were comparable to those of the reference.
A minor difference in colour was detected between the reference and the enriched spread but without affecting negatively the quality of the spread.

The invention claimed is:

1. A food supplement consisting essentially of an isolated hydroquinone substituted polyunsaturated fatty acid, obtained from kombo nut oil or a food acceptable derivative of said acid selected from the group consisting of a C1 to C32 acid ester or alcohol ester of said acid and food acceptable salts of said acid, said supplement being in the form of a powder, granules or an encapsulate and wherein the acid or derivative of said acid is present in an amount of 2 to 95 wt % of said supplement.

2. The food supplement according to claim 1 in an encapsulated form wherein the encapsulating material is selected from the group consisting of gelatin, starch, modified starch, flour, modified flour, sucrose, lactose, glucose and fructose.

3. The food supplement according to claim 1 wherein the hydroquinone substituted polyunsaturated fatty acid is sargahydroquinoic acid (SHQA) or a food acceptable derivative thereof selected from a C1 to C32 acid or alcohol ester of said acid and food acceptable salts of said acid.

4. The food supplement of claim 3 wherein the derivative is an acid ester of SHQA having 6 to 20 carbon atoms.

5. The food supplement of claim 3 wherein the derivative is an alcohol ester of SHQA having 6 to 20 carbon atoms.

6. The food supplement of claim 3 wherein the food acceptable salt of the hydroquinone substituted poly unsaturated fatty acid derivative is a Na or K or Ca salt of SHQA.

7. A composition comprising the food supplement of claim 1 further comprising an effective amount of one or more antioxidants selected from the group consisting of natural or synthetic tocopherols, butylated hydroxy toluene (BHT), tert-butylhydroquinone (TBHQ), butylated hydroxy anisole (BHA), propylgallate, free radical scavengers, enzymes with antioxidant properties and ascorbyl esters of fatty acids.

8. The food supplement of claim 3 wherein the alcohol component of the ester contains 14 to 18 carbon atoms.

9. The food supplement according to claim 1 wherein the hydroquinone substituted poly unsaturated fatty acid is SHQA.

* * * * *

UNITED STATES PATENT AND TRADEMARK OFFICE
CERTIFICATE OF CORRECTION

PATENT NO. : 7,582,317 B2 Page 1 of 1
APPLICATION NO. : 10/230352
DATED : September 1, 2009
INVENTOR(S) : Barclay et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1458 days.

Signed and Sealed this

Fourteenth Day of September, 2010

David J. Kappos
*Director of the United States Patent and Trademark Office*